US006896665B2

(12) United States Patent
Picha et al.

(10) Patent No.: US 6,896,665 B2
(45) Date of Patent: May 24, 2005

(54) GASTROSTOMY DEVICE PACKAGE AND METHOD OF ASSEMBLY

(75) Inventors: George J. Picha, Independence, OH (US); Davor G. Mandic, Cleveland Heights, OH (US)

(73) Assignee: Applied Medical Research, Cleveland, OH (US)

( * ) Notice: Subject to any disclaimer, the term of this patent is extended or adjusted under 35 U.S.C. 154(b) by 199 days.

(21) Appl. No.: 10/016,532

(22) Filed: Dec. 10, 2001

(65) Prior Publication Data

US 2003/0109830 A1 Jun. 12, 2003

(51) Int. Cl.[7] .............................................. A61M 29/00
(52) U.S. Cl. ........................................ 604/104; 604/174
(58) Field of Search ......................... 604/174, 104–106, 604/107, 109, 96.01, 270; 606/198

(56) References Cited

U.S. PATENT DOCUMENTS

| | | | |
|---|---|---|---|
| 1,926,608 | A | 9/1933 | Ziegler |
| 3,640,269 | A | 2/1972 | Delgado |
| 4,315,513 | A | 2/1982 | Nawash et al. |
| 4,393,873 | A | 7/1983 | Nawash et al. |
| 4,571,241 | A | 2/1986 | Christopher |
| 4,666,433 | A | 5/1987 | Parks |
| 4,685,901 | A | 8/1987 | Parks |
| 4,701,163 | A | 10/1987 | Parks |
| 4,798,592 | A | 1/1989 | Parks |
| 4,986,810 | A | 1/1991 | Semrad |
| 5,002,572 | A | 3/1991 | Picha |
| 5,007,900 | A | 4/1991 | Picha et al. |
| 5,084,014 | A | 1/1992 | Picha et al. |
| 5,125,897 | A | 6/1992 | Quinn et al. |
| 5,234,457 | A | 8/1993 | Andersen |
| 5,267,982 | A | 12/1993 | Sylvanowicz |
| 5,308,325 | A | 5/1994 | Quinn et al. |
| 5,336,203 | A | 8/1994 | Goldhardt et al. |
| 5,356,391 | A | 10/1994 | Stewart |
| 5,366,504 | A | 11/1994 | Andersen et al. |
| 5,391,159 | A | 2/1995 | Hirsch et al. |
| 5,413,565 | A | 5/1995 | Michels et al. |
| 5,439,444 | A | 8/1995 | Andersen et al. |
| 5,549,657 | A | 8/1996 | Stern et al. |
| 5,919,231 | A | 7/1999 | Blom et al. |
| 5,941,855 | A | 8/1999 | Picha et al. |

*Primary Examiner*—LoAn H. Thanh
(74) *Attorney, Agent, or Firm*—Pearne & Gordon LLP

(57) ABSTRACT

A gastrostomy device includes a tubular portion and an internal bolster having a radial wing secured to the tubular portion. The internal bolster is flexible and permits elastic deformation between a first orientation with the wing wrapped into a generally cylindrical configuration and a second orientation with the wing unfuried. A constraining member encases the internal bolster to retain the internal bolster in the first orientation and to cover at least a major portion of the wrapped wing. Removal of the casing permits the internal bolster to move from the first orientation to the second orientation. The internal bolster may be deployed by a ripcord, freeing the internal bolster into the patient' stomach and deploying the internal bolster to the second orientation. Alternatively, the internal bolster may be deployed by the constraining member being dissolved by the patient's bodily fluids located inside the patient's stomach.

9 Claims, 5 Drawing Sheets

GASTROSTOMY DEVICE PACKAGE AND METHOD OF ASSEMBLY

BACKGROUND OF THE INVENTION

This invention relates generally to a gastrostomy feeding device and specifically, to a novel and improved gastrostomy feeding device for deploying an internal bolster into a patient's stomach where a constraining member that encases the internal bolster takes the form of either a dissolvable capsule that is deployed using a ripcord or a sacrificial tape wrapping.

There are many medical applications in which a device or substance must be contained or constrained prior to placement in the body. Methods commonly used to insert non-balloon type entral feeding devices result in excessive patient discomfort.

It is known that devices are available for supplying food and/or medication to a patient within the stomach. For example, U.S. Pat. No. 4,666,433 discloses such a gastrostomy feeding device that is inserted through a stoma and into the patient's stomach. The '433 device is secured in place by an inflatable balloon or mushroom tip within the stomach, and by an adjustable ring on the abdominal wall.

U.S. Pat. No. 5,941,855, which is included herein in its entirety by reference, discloses a gastrostomy device having a tubular portion, first and second fingers, a rod member and a suture member. The rod member and suture member cooperate to releasably retain the fingers in an installation configuration for insertion through a patient's stomach. Following insertion, the rod member and suture member release the fingers to permit the fingers to move to a deployed configuration. In the installation configuration, the fingers are generally in line with an axis of the tubular portion while, in the deployed configuration, the fingers are generally transverse to the tubular portion axis.

It is also known that emplacement of a gastrostomy tube is simplified by compressing the enlarged end into a capsule or binding of a material that dissolves in the body. U.S. Pat. No. 4,393,873 discloses a gastrostomy tube packaged for insertion using a gelatin capsule technique. The head is compressed and wrapped or bound in a soluble suture thread or other web or thread made of a material which is soluble in the stomach.

Certain medical devices called stents are well known and have a variety of forms. U.S. Pat. No. 5,234,457 discloses a stent which is maintained in a collapsed condition by a dissolvable material. When the stent is placed in a vessel and bounded by a vessel wall, the material changes from a solid to a liquid to permit the stent to expand into the vessel wall.

Although it is common in the art to use the medical devices described above, the present invention improves upon them by providing a technique wherein a dissolvable member and a ripcord are combined onto a gastrostomy feeding device. The ease and comfort of the patient improves greatly using the present invention and the ripcord gives the caregiver an immediate and positive indication that the internal bolster has been released into the patient's body unlike the prior art devices.

SUMMARY OF THE INVENTION

The present invention is directed to a percutaneous gastrostomy device comprising, a tubular portion defining a longitudinal axis, an internal bolster having a radial wing secured to the tubular portion, the internal bolster being flexible to permit elastic deformation between a first orientation generally aligned with the longitudinal axis, with the wing wrapped into a generally cylindrical configuration and a second orientation with the wing unfurled and extending generally transverse to the tubular portion longitudinal axis and a constraining member encasing the internal bolster to retain the internal bolster in the first orientation, with the wing wrapped into the generally cylindrical configuration, and to cover at least a major portion of the wrapped wing, wherein the removal of the casing permits the internal bolster to move from the first orientation to the second orientation.

In accordance with one aspect of this invention, a method and apparatus is provided to constrain a medical device or substance in a dissolvable material and release it inside the body.

In accordance with another aspect of this invention, a novel and improved medical device packaging and delivery method is provided.

In accordance with still another aspect of this invention, the novel and improved medical delivery method has a wide range of applications including, but not limited to, catheters, stents, invasive radiology, etc.

In normal operation of the illustrated embodiment, this invention gives the care giver a positive indication that the device has been released.

These and other aspects of this invention are illustrated in the accompanying drawings, and are more fully disclosed in the following specification.

DESCRIPTION OF THE INVENTION

Figure 1:
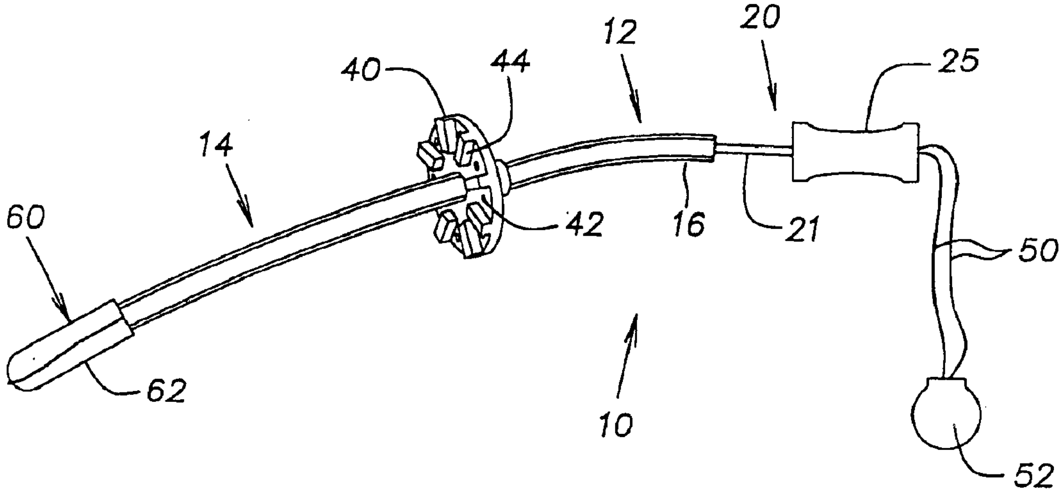
FIG. 1 is a perspective view of the gastrostomy feeding device with a capsuled constraining member and ripcord according to one aspect of the present invention.
Figure 1A:
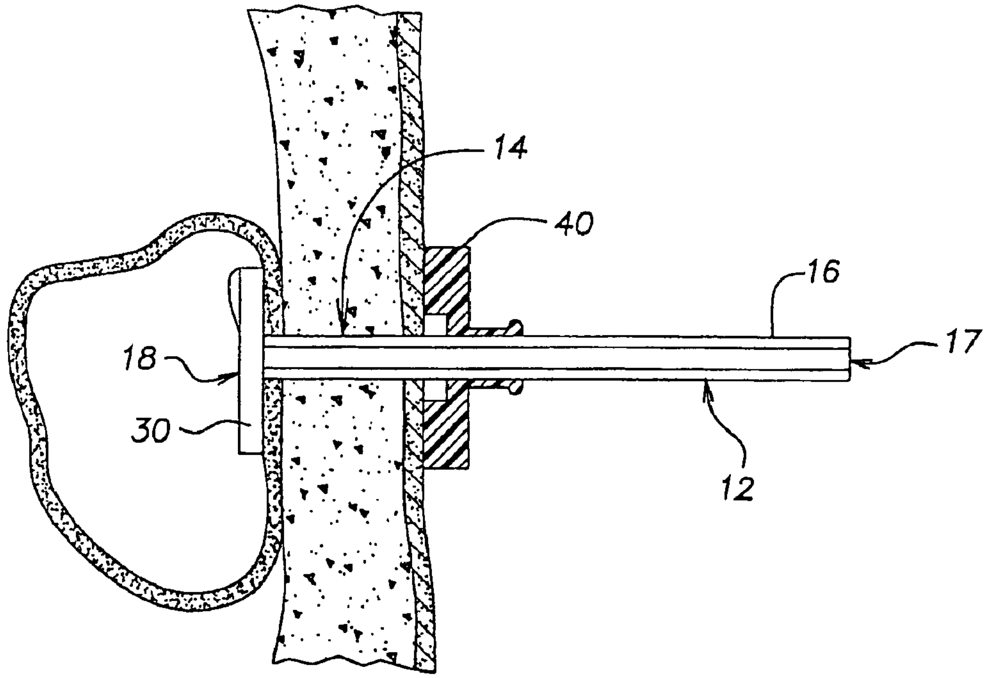
FIG. 1A is a perspective view of the gastrostomy feeding device according to the present invention deployed and installed in a patient's stomach.

With reference to the drawing figures, a gastrostomy device 10 and a method of assembling the device 10 is illustrated. The gastrostomy device 10 with dissolvable capsule and ripcord is illustrated in FIG. 1. As shown in FIG. 1A, once deployed, the gastrostomy device consists of a proximal extension 12 positioned outside the body and a distal extension 14 positioned within the body.

The gastrostomy device 10 is inserted inside the body and positioned on the patient's abdomen by an adjustable silicone locking ring 40. As shown in FIGS. 1 and 1A, the locking ring 40 is provided with a plurality of vent holes 42 and circular ridges 44 to permit air to contact the entry to the body and reduce infection and irritation. Use of the ring 40, prevents the gastrostomy device 10 from being drawn into the body.

The gastrostomy device 10 includes a tubular portion 16 having a distal end 18 and a proximal end 17. The distal end 18 has an internal bolster 30 secured thereto. The tubular portion 16 and the internal bolster 30 may be integrally molded together from a bio-compatible material, such as a silicone rubber.

Figure 2:
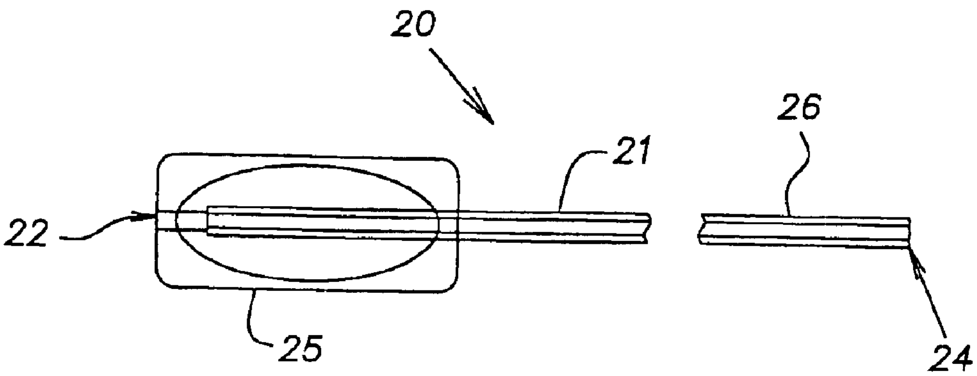
FIG. 2 illustrates a rod member assembly according to the present invention.

Referring to FIG. 2, rod member 20 comprises a hollow tube 21 having a proximal end 22 and a distal end 24. The rod member 20 is positioned inside the tubular portion 16 of device 10, as will be discussed more fully hereinafter. As shown in FIG. 2, the rod member 20 is hollow along its longitudinal axis and includes a handle 25 at its proximal end 22.

Figure 3:
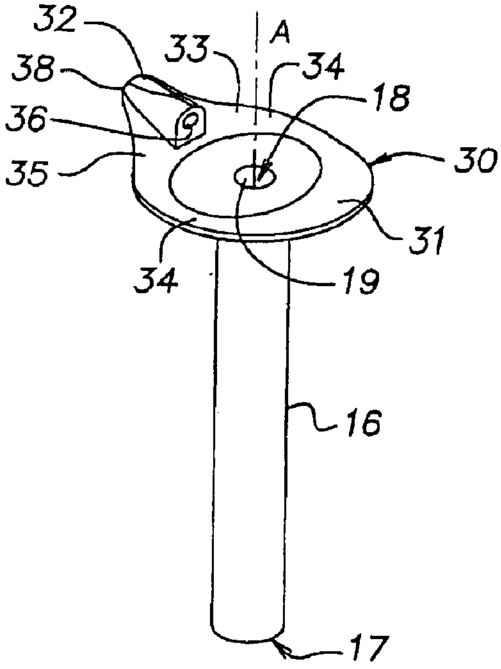
FIG. 3 illustrates an internal bolster secured to a tubular portion.

Referring to FIG. 3, an internal bolster 30 has a first part 31 and a second part 33. The first and second parts 31, 33 cooperate to provide lateral regions 34. The lateral regions 34 are secured in a deformed condition when the internal bolster 30 is in an installed configuration.

The first part 31 of the internal bolster 30 is generally semi-oval. The second part 33 of the bolster is integrally connected to the first part and defines a radial wing 35. The radial wing 35 includes, on its outer surface, a pocket 32 for receipt of the rod member 20 (FIG. 2) to permit deformation of the internal bolster 30 from a first orientation, to a second orientation, as will be discussed more fully hereinafter.

With specific reference to FIG. 3, the tubular portion 16 includes a proximal end 17, through which food is fed and a distal end 18 that is positioned within the body for insertion in a patient's stoma. The internal bolster 30 is located on the distal end 18 of tubular portion 16. A pocket 32 for receipt of the proximal end 24 of the rod member 20 (FIG. 2) is also located on the internal bolster 30.

Figure 3A:
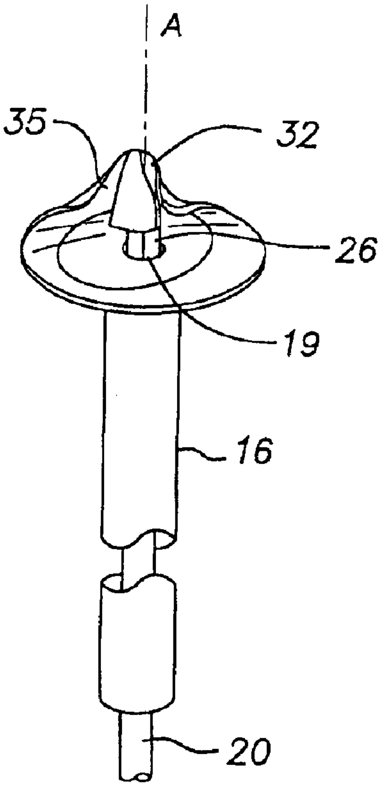
FIG. 3A illustrates the internal bolster secured to a tubular portion and the rod member's distal end received within a pocket of the internal bolster.

With specific reference to FIG. 3A, the rod member 20 extends within the tubular portion 16 and includes a projecting end 26 that extends beyond the tubular portion opening 19 at the distal end 18 of the tubular portion. The rod member projecting end 26 is removably inserted into the pocket 32 provided on the radial wing 35. As shown in FIG. 3A, the radial wing 35 of the internal bolster 30 is bent or deformed by the rod member 20 to be in-line with an axis A of the tubular portion 16, as illustrated.

Figure 3B:
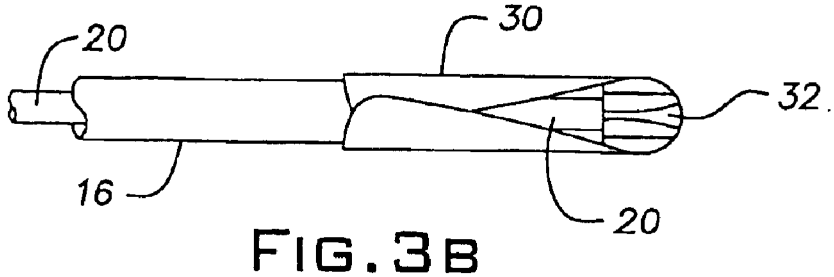
FIG. 3B illustrates the internal bolster secured to a tubular portion and the rod member's distal end received within a pocket of the internal bolster and the internal bolster folded around the tubular portion.

As shown in FIG. 3B, the internal bolster 30 is folded around the distal end 18 of the feeding tube 16, therefore allowing the internal bolster 30 to be inserted inside a capsule as will be discussed more fully hereinafter.

Figure 4:
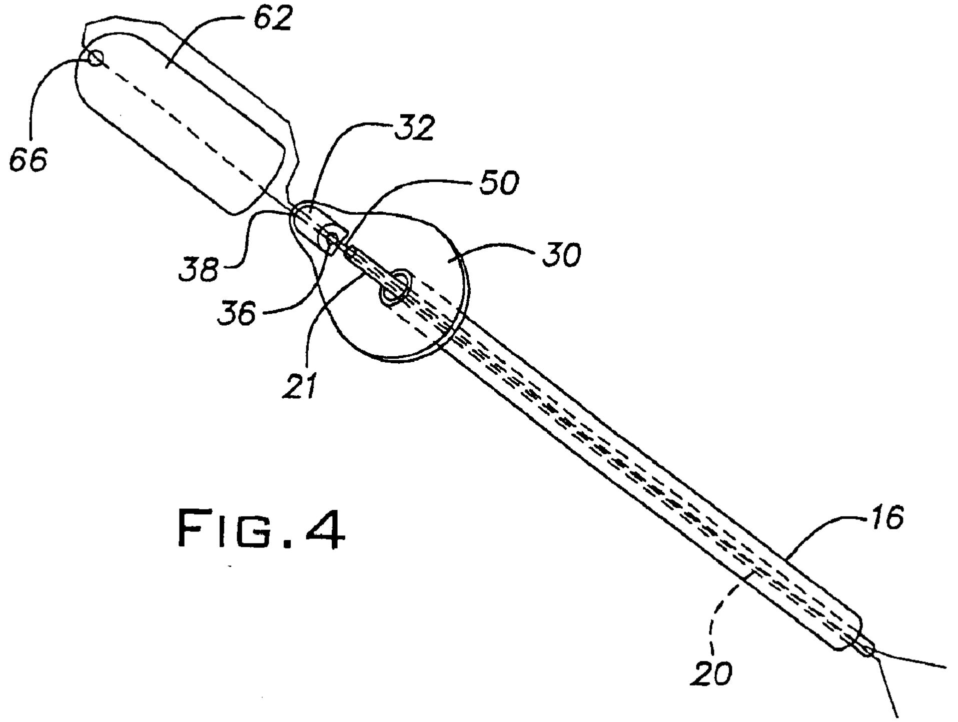
FIG. 4 is an exploded view showing the internal bolster and a single loop ripcord deployment method.

Referring now to FIG. 4, a capsule 62 encases the internal bolster to retain the internal bolster 30 in the first orientation, with the wing wrapped into a generally cylindrical configuration and to cover at least a major portion of the wrapped wing. The constraining member may be in the form of a capsule 62. The capsule 62 is formed into a hollow tubular shape with one open end and one end rounded to a hemispherical shape. On the rounded end of the capsule 62 is located a hole 66 through which a ripcord 50 is threaded as will be described in further detail below. The capsule 62 is located on the distal extension 14 of the gastrostomy device 10. The capsule 62 is placed over the folded internal bolster 30 as shown in FIG. 4. The capsule 62 maintains the internal bolster 30 in its folded position until the gastrostomy device 10 is deployed inside of the body.

Figure 4A:
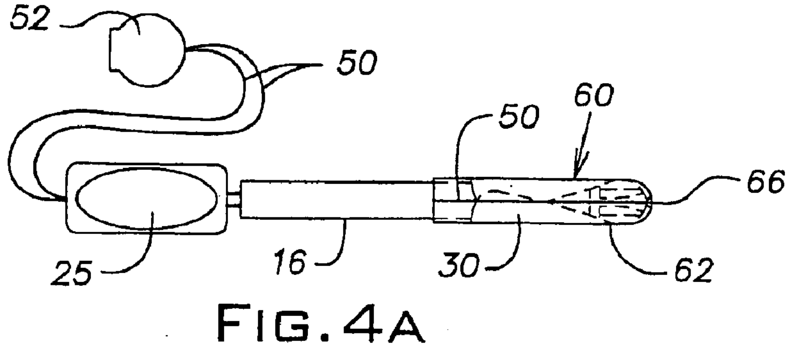
FIG. 4A illustrates the internal bolster folded with the rod member installed and with a capsule constraining member and single loop ripcord deployment method.

The gastrostomy feeding device 10 as described, employs a ripcord 50. The ripcord 50, as shown in FIG. 4A, is provided with a pull tab 52. The ripcord 50 is threaded through the hollow tube 21, through the opening 36 in pocket 32 (FIG. 4) on internal bolster 30, through the passage in the pocket, and out through pocket exit hole 38, through capsule 62, through hole 66 in the capsule, along the sidewall of the capsule and back through pocket exit hole 38 and back through hollow tube 21. Both ends of the ripcord 50 extend through the handle 25 of rod member 20 and are fastened to a pull tab 52. The pull tab 52 is positioned at the proximal extension 12 of the completed gastrostomy feeding device 10.

Figure 5:
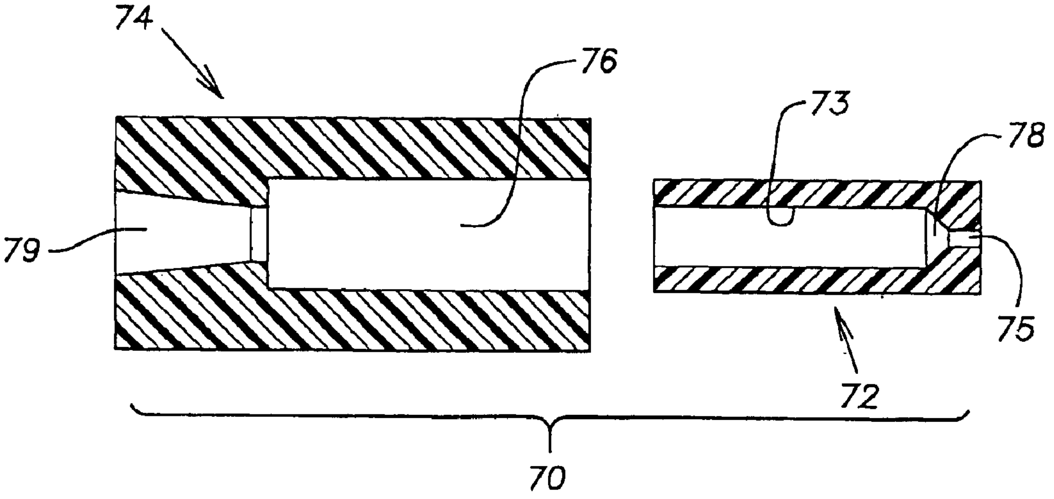
FIG. 5 illustrates the capsule loading fixtures according to the present invention.

Referring now to FIG. 5, an assembly fixture 70 includes a capsule holder 72 and funnel 74, employed to assemble a folded internal bolster 30 inside of the capsule 62. The capsule holder 72 is a rigid cylindrical body containing a cylindrical recess 73 for accommodating an empty capsule 62 and an air pocket relief aperture 75 at the end section 78 of the cylinder recess 73. The funnel 74 is defined by a conical recess 79 at one end, and cylindrical recess 76 at the other end. During assembly, the capsule 62 (FIG. 7) is placed in the capsule holder 72. The capsule holder 72 is then fitted into the cylindrical recess 76 of funnel 74, and the conical shape of conical recess 79 acts as a funnel to guide the internal bolster 30 into the open end of the capsule 62.

Figure 6:
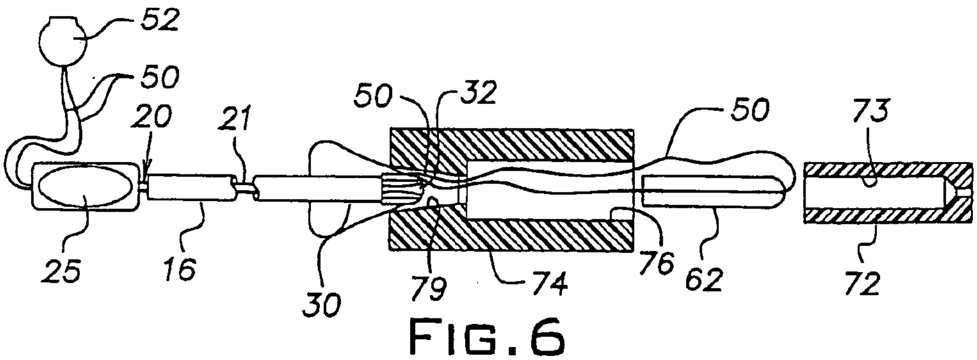
FIG. 6 is an exploded view showing the installation of the ripcord into the capsule and through the assembly fixture according to the present invention.

Referring now to FIG. 6, the assembly of the gastrostomy 10 device with the dissolvable capsule 62 and the ripcord 50 will now be described. The rod member 20 is inserted into the end of the tube 16, and out through the hole in the center of the internal bolster 30 and into the pocket 32.

Figure 7:
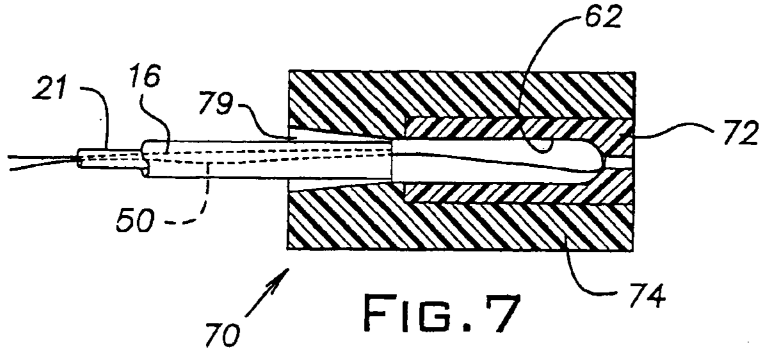
FIG. 7 illustrates the capsule with ripcord in the assembly fixture according to one aspect of the present invention.

A length of ripcord 50 is threaded through a hole 66 (FIG. 4) located in the end of capsule 62. Both ends of the ripcord 50 are then threaded through the funnel 74 (FIG. 6) of assembly fixture 70, through pocket 32 on internal bolster 30 (FIG. 4), though the hollow tube 21, and through the handle 25 and fastened to the pull tab 52. The capsule 62 and ripcord 50 are then inserted into the assembly fixture 70 as shown in FIG. 7. The sides of the internal bolster 30 are folded by the conical recess 79 as the rod member 20 and ripcord 50 are inserted into the assembly fixture 70 and into the capsule to the position shown in FIG. 7.

The feeding tube assembly, as shown in FIG. 4, is removed from the assembly fixture 70 with the folded internal bolster 30 contained inside the capsule 62 and the ripcord 50 exposed.

Figure 8:
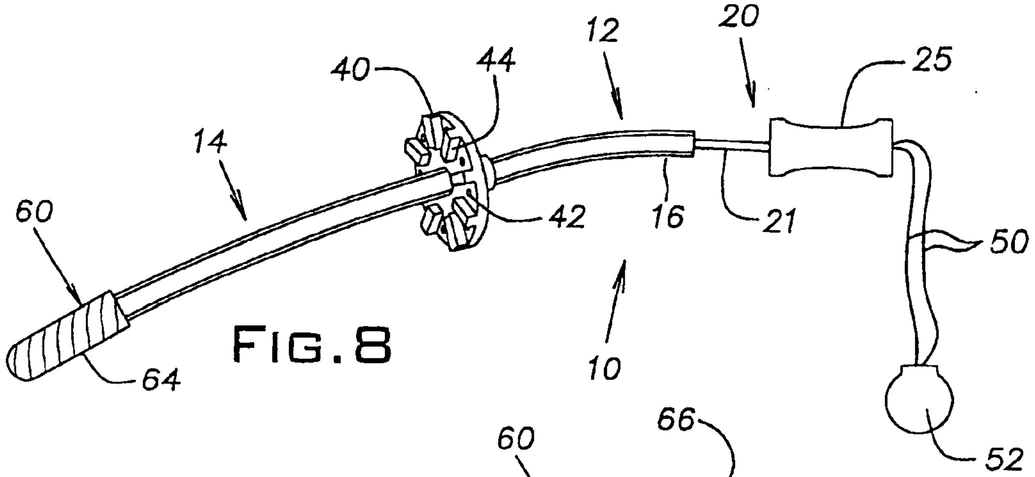
FIG. 8 illustrates an alternate embodiment of the gastrostomy feeding device with a wrapped constraining member.

The constraining member 60 may also be a wrapping 64 as shown in FIG. 8. The wrapping 64 acts to contain the internal bolster 30 in its folded position in a similar way as is achieved with the capsule 62. Prior to assembly, the wrapping 64 is in the form of a long narrow strip. The strip of wrapping is manually wrapped about the folded internal bolster 30 to secure it in the folded position for insertion into the body. The wrapping forms the constraining member 60 around the folded internal bolster 30 in any thickness, shape or manner desired. A ripcord 50 may also be employed with the wrapper in a manner similar to that of the capsule 62 as discussed above as the first embodiment for deployment. The capsule 62 or wrapping 64 may be made of a material such as vegetable cellulose (HPMC). The material is such that upon insertion of the capsule or wrapping inside the body, the capsule 62 or wrapping 64 may dissolve inside the body.

One technique for emplacement of the gastrostomy device 10 is to insert the distal end 14 of the gastrostomy device through the stoma and into the stomach. The constraining member 60 (either the capsule 62 or the wrapping 64) is released by grasping the handle 25 with one hand and pulling the tab 52 of the ripcord 50 with the other hand. This action tightens up the loop in the ripcord 50 to tear through the sidewall of the constraining member 60. The projecting member 26 of the rod is withdrawn from the pocket 32 by grasping the proximal extension 12 of the device 10 and pulling the handle 25. This frees the bolster 30 and the bolster returns to its original shape as illustrated in FIG. 1A. The torn member 60 then dissolves inside the body.

Another technique for emplacement of the gastrostomy device 10 is to insert the distal end 14 of the gastrostomy device through the stoma and into the stomach and then the constraining member 60 (either the capsule 62 or the wrapping 64) is released by the dissolution of the constraining member by the patient's bodily fluids located inside the patients stomach to free the bolster 30. The constraining member 60 is made of a material dissolvable in the patient's stomach at a temperature range of between 50–100 degree F.

Using this technique, the ripcord 50 acts as a deployment indicator, when the ripcord can be withdrawn with little or no resistance, the bolster 30 has returned to its original shape as illustrated in FIG. 1A.

Figure 9:
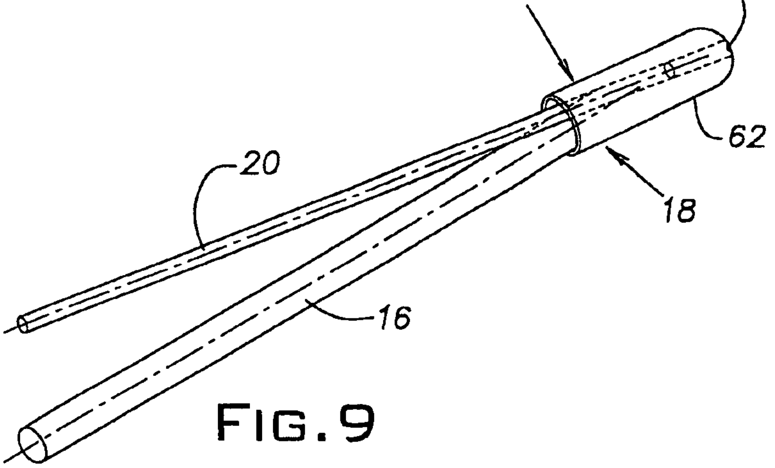
FIG. 9 illustrates a partial perspective view of an alternate embodiment of the gastrostomy with the rod member outside the tubular portion and with a wrapped constraining member.

With specific reference to FIG. 9, a partial perspective view of an alternate embodiment of the present invention is shown where the rod member 20 preferably extends alongside and generally parallel to the tubular portion 16 at the distal end 18 of the gastrostomy device 10. In this alternative embodiment, the constraining member 60 may be either a wrapping 64 or a capsule 62 and will operate as described above in the previous embodiment. In addition, the emplacement technique to free the bolster 30 may be either by the use of a ripcord 50 or from the dissolution of the constraining member 60 by the patient's bodily fluids located inside the patient's stomach as described above in the previous embodiment.

When using the dissolution technique, the time necessary for dissolution of the constraining member 60 may be controlled by injecting a diluent, such as water, through the tube 16. The diluent travels along axis A (FIG. 3) and into the capsule 62 (FIG. 4), out of the hole 66 and into the patient's stomach (FIG. 1A). Controlling how and when the dissolution takes place may be achieved in a number of ways, for example, by varying the dissolution temperature of the constraining member, by varying the molecular weight and degree of hydrolysis of the diluent, by varying the rate of diluent delivery, and by varying the amount of exposed surface area used on the constraining member.

Figure 10:
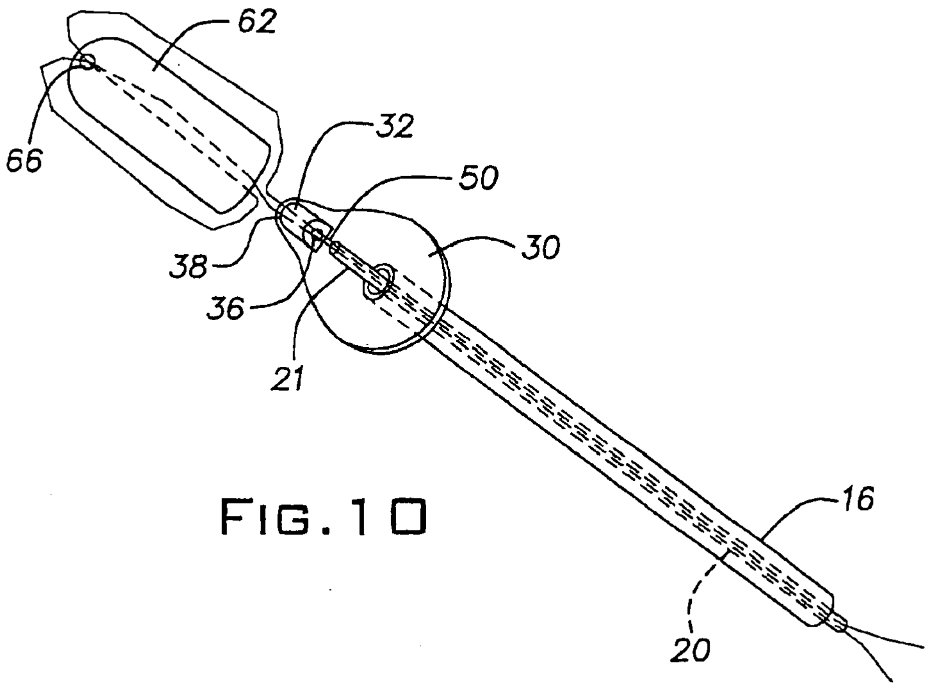
FIG. 10 illustrates an exploded view showing the internal bolster and a double loop ripcord deployment method
Figure 11:
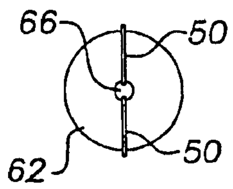
FIG. 11 is an end view of the capsule using the double loop deployment method for the ripcord of the present invention.

With specific reference to FIG. 10, the ripcord is shown using a double loop deployment arrangement. In using the double loop arrangement, the ripcord 50 is laced though the capsule 62 twice. The exposed ripcords are positioned 180 degrees apart (FIG. 11) and when the ripcord 50 is pulled, the capsule is cut into two halves. The emplacement technique to free the bolster 30 in the double loop arrangement may be either by the use of a ripcord 50 or from the dissolution of the constraining member 60 by the patient's bodily fluids. In addition, in the double loop arrangement as shown in FIG. 12, the ripcord 50 can exit the tube 16 through hollow tube 21 of rod member 20 (path I as illustrated in FIG. 12) or through the end of the tube 16 (path O as illustrated in FIG. 12).

Figure 12:
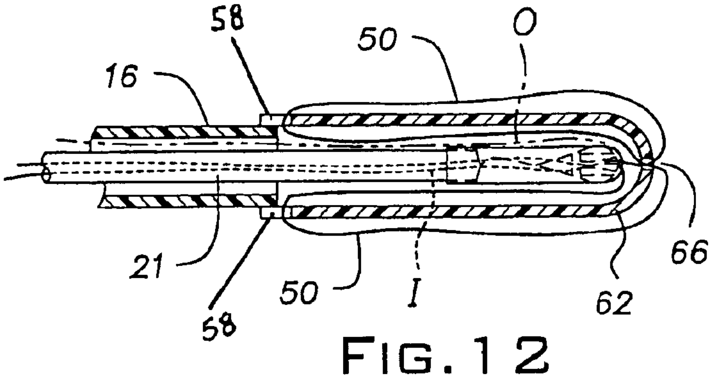
FIG. 12 illustrates the gastrostomy feeding device having a double loop ripcord arrangement according to an aspect of the present invention.
Figure 10A:
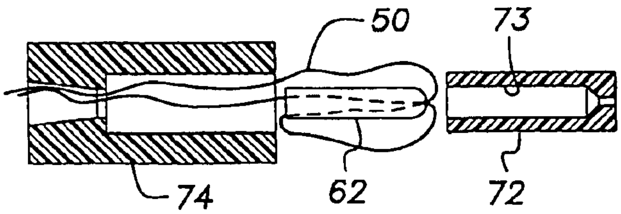
FIG. 10A illustrates the gastrostomy device folded with the rod member installed and with a capsule constraining member and double loop ripcord deployment method.

In addition as shown in FIG. 12, the ripcord 50 as it loops in either the double loop or single loop arrangement around capsule 62 engages in a slot section 58 that enables the ripcord to tightly fit along the outside of capsule 62.

Although the invention has been shown and described with respect to a certain embodiment, it is obvious that equivalent alterations and modifications will occur to others skilled in the art upon reading and understanding of the specification. The present invention includes all such equivalent alterations and modifications, and is limited only by the scope of the claims.

What is claimed is:

1. A percutaneous gastrostomy device comprising:

a tubular portion having a distal end;

an internal bolster secured to said distal end, said internal bolster having a radial wing secured to said tubular portion, said internal bolster being flexible to permit elastic deformation between a first orientation generally aligned with said longitudinal axis, with the wing wrapped into a generally cylindrical configuration and a second orientation with the wing unfuried and extending generally transverse to said tubular portion longitudinal axis, said wing including a pocket;

a rod member, a projecting end and a handle, said rod member having a hollow tube along its logitudinal axis, said rod member being removably received within said tubular portion and said projecting end being removably received within said pocket of said internal bolster; and a constraining member encasing said internal bolster to retain said internal bolster in said first orientation, with said wing wrapped into said generally cylindrical configuration and to cover at least a major portion of said wrapped wing, said constraining member having a ripcord attached thereto for tearing said constraining member and deploying said internal bolster, allowing said internal bolster to move from said first orientation to said second orientation.

2. The percutaneous gastrostomy device according to claim 1, wherein the constraining member encasing said internal bolster is in the form of a capsule having an axial hole therein.

3. The percutaneous gastrostomy device as set forth in claim 2, wherein said ripcord is threaded through the hollow tube, through an opening in a pocket on the internal bolster, through a passage in the pocket, and out through a pocket exit hole, through the capsule, through a hole in the capsule, along the sidewall of the capsule and back through the pocket exit hole and back through the hollow tube, both ends of the ripcord extending through a handle of the rod member and both ends are fastened to a pull tab.

4. The percutaneous gastrostomy device as set forth in claim 3, wherein said ripcord is threaded through said the hole located in said capsule and along a side of a wall of said capsule and positioned to tear said capsule wall.

5. The percutaneous gastrostomy device as set forth in claim 3, wherein said ripcord is threaded twice through said hole located in said capsule and along each side wall of said capsule to tear said capsule walls.

6. The percutaneous gastrostomy device as set forth in claim 2, wherein said capsule is made of a material dissolvable in the patient's stomach.

7. The percutaneous gastrostomy device as set forth in claim 1, wherein a locking ring is positioned medially along the tubular portion, and sized to frictionally engage the tubular portion, and slidably mounted there along, and adjustable solely by frictional engagement with the tubular portion to accommodate to the size of the wearer, the locking ring providing a plurality of perforations and spaced ridges to enable air circulation between the locking ring and the body.

8. A percutaneous gastrostomy device comprising:

a tubular portion defining a longitudinal axis;

an internal bolster having a single radial wing secured to said tubular portion, said internal bolster being flexible to permit elastic deformation between a first orientation generally aligned with said longitudinal axis, with the wing wrapped into a generally cylindrical configuration and a second orientation with the wing unfuried and extending generally transverse to said tubular portion longitudinal axis; and a constraining member encasing said internal bolster to retain said internal bolster in said first orientation, with said wing wrapped into said generally cylindrical configuration, and to cover at least a major portion of said wrapped wing, wherein the removal of said constraining member permits the internal bolster to move from said first orientation to said second orientation, wherein the constraining member encasing said internal bolster is in the form of a capsule, and wherein said capsule is made of a material dissolvable in the patient's stomach.

9. A percutaneous gastrostomy device comprising:

a tubular portion defining a longitudinal axis;

an internal bolster having a single radial wing secured to said tubular portion, said internal bolster being flexible to permit elastic deformation between a first orientation generally aligned with said longitudinal axis, with the wing wrapped into a generally cylindrical configuration and a second orientation with the wing unfuried and extending generally transverse to said tubular portion longitudinal axis; and a constraining member encasing said internal bolster to retain said internal bolster in said first orientation, with said wing wrapped into said generally cylindrical configuration, and to cover at least a major portion of said wrapped wing, wherein the removal of said constraining member permits the internal bolster to move from said first orientation to said second orientation, wherein a locking ring is positioned medially along the tubular portion, and sized to frictionally engage the tubular portion, and slidably mounted there along, and adjustable solely by frictional engagement with the tubular portion to accommodate to the size of the wearer, the locking ring providing a plurality of perforations and spaced ridges to enable air circulation between the locking ring and the body.

* * * * *

UNITED STATES PATENT AND TRADEMARK OFFICE

CERTIFICATE OF CORRECTION

PATENT NO. : 6,896,665 B2
DATED : May 24, 2005
INVENTOR(S) : Picha et al.

It is certified that error appears in the above-identified patent and that said Letters Patent is hereby corrected as shown below:

Title page, Item [54] and Column 1, lines 1-2,
Title, please delete "GASTROSTOMY DEVICE PACKAGE AND METHOD OF ASSEMBLY", and insert therefor -- PERCUTANEOUS GASTROSTOMY DEVICE --.

Title page,
Item [56], References Cited, U.S. PATENT DOCUMENTS, please insert reference -- 5,279,564A 1/1994 Taylor 604/104 --.
Item [57], ABSTRACT,
Line 6, please delete "unfuried", and insert therefor -- unfurled --.
Line 12, please delete "patient'", and insert therefor -- patient's --.

Column 6,
Line 39, please delete "unfuried", and insert therefor -- unfurled --.

Column 7,
Line 32, please delete "unfuried", and insert therefor -- unfurled --.

Column 8,
Line 17, please delete "unfuried", and insert therefor -- unfurled --.

Signed and Sealed this

Twentieth Day of September, 2005

JON W. DUDAS
*Director of the United States Patent and Trademark Office*